(12) United States Patent
Bhumiratana et al.

(10) Patent No.: US 12,714,580 B2
(45) Date of Patent: Aug. 25, 2026

(54) SYSTEMS, KITS, AND DEVICES FOR DRILLING ARTICULAR CARTILAGE AND METHODS THEREOF

(71) Applicant: EPIBONE, INC., Long Island City, NY (US)

(72) Inventors: Sarindr Bhumiratana, Oceanside, NY (US); Keith Yeager, Springfield, NJ (US); Brian Mckellar, Exton, PA (US); Angela Huang, Flushing, NY (US); Eric Meade Jeffries, Warrington, PA (US)

(73) Assignee: EPIBONE, INC., Long Island City, NY (US)

( * ) Notice: Subject to any disclaimer, the term of this patent is extended or adjusted under 35 U.S.C. 154(b) by 885 days.

(21) Appl. No.: 17/918,858

(22) PCT Filed: Apr. 9, 2021

(86) PCT No.: PCT/US2021/026564
§ 371 (c)(1),
(2) Date: Oct. 13, 2022

(87) PCT Pub. No.: WO2021/211372
PCT Pub. Date: Oct. 21, 2021

(65) Prior Publication Data

US 2023/0225883 A1 Jul. 20, 2023

Related U.S. Application Data

(60) Provisional application No. 63/009,576, filed on Apr. 14, 2020.

(51) Int. Cl.
*A61F 2/46* (2006.01)
*A61B 17/00* (2006.01)
(Continued)

(52) U.S. Cl.
CPC ........ *A61F 2/4618* (2013.01); *A61B 17/1615* (2013.01); *A61B 17/162* (2013.01);
(Continued)

(58) Field of Classification Search
CPC ..... A61B 17/1633; A61B 17/00; A61B 17/16; A61B 17/1613; A61B 17/1615;
(Continued)

(56) References Cited

U.S. PATENT DOCUMENTS 5,324,300 A 6/1994 Elias et al.
5,810,828 A 9/1998 Lightman et al.
(Continued)

OTHER PUBLICATIONS

International Search Report and Written Opinion issued in PCT/US2021/026564 dated Jul. 7, 2021.

*Primary Examiner* — Marcela I. Shirsat
(74) *Attorney, Agent, or Firm* — Troutman Pepper Locke LLP

(57) ABSTRACT

Drilling devices, systems, kits and methods for drilling cartilage defects are disclosed. A system includes a handle device having an adjustable shaft collar rotatable to adjust a drill set distance between the adjustable shaft collar and the handle. The handle device can include a distal drill guide extending from the handle at an end opposite the adjustable shaft collar. The system includes a drill collar attachable to a drill bit and configured to remain stationary along a length of the drill bit once attached. The system includes a rotatable disk positionable between the adjustable shaft collar and the drill collar. The rotatable disk can include a central hole sized to accept the drill bit.

45 Claims, 12 Drawing Sheets

(51) Int. Cl.

| | |
|---|---|
| ***A61B 17/16*** | (2006.01) |
| ***A61B 17/17*** | (2006.01) |
| ***A61B 17/56*** | (2006.01) |
| ***A61B 90/00*** | (2016.01) |

(52) U.S. Cl.
CPC ...... *A61B 17/1622* (2013.01); *A61B 17/1633* (2013.01); *A61B 17/17* (2013.01); *A61B 17/00* (2013.01); *A61B 2017/00424* (2013.01); *A61B 2017/0046* (2013.01); *A61B 17/16* (2013.01); *A61B 17/1613* (2013.01); *A61B 17/1617* (2013.01); *A61B 17/1624* (2013.01); *A61B 17/1631* (2013.01); *A61B 17/1635* (2013.01); *A61B 17/1637* (2013.01); *A61B 17/1695* (2013.01); *A61B 17/1697* (2013.01); *A61B 17/56* (2013.01); *A61B 2017/564* (2013.01); *A61B 90/00* (2016.02); *A61B 2090/036* (2016.02); *A61B 2090/061* (2016.02); *A61F 2/46* (2013.01)

(58) Field of Classification Search
CPC . A61B 17/1617; A61B 17/1622; A61B 17/17; A61B 17/56; A61B 17/162; A61B 17/1624; A61B 17/1631; A61B 17/1635; A61B 17/1637; A61B 17/1695; A61B 17/1697; A61B 2017/564; A61B 2017/00424; A61B 2017/0046; A61B 90/00; A61B 2090/036; A61B 2090/061; A61F 2/4618; A61F 2/46
USPC ........................................................... 606/80
See application file for complete search history.

(56) References Cited

U.S. PATENT DOCUMENTS

2014/0276880 A1 9/2014 Li
2015/0257769 A1 9/2015 Papenfuss
2017/0266736 A1 9/2017 Ohana

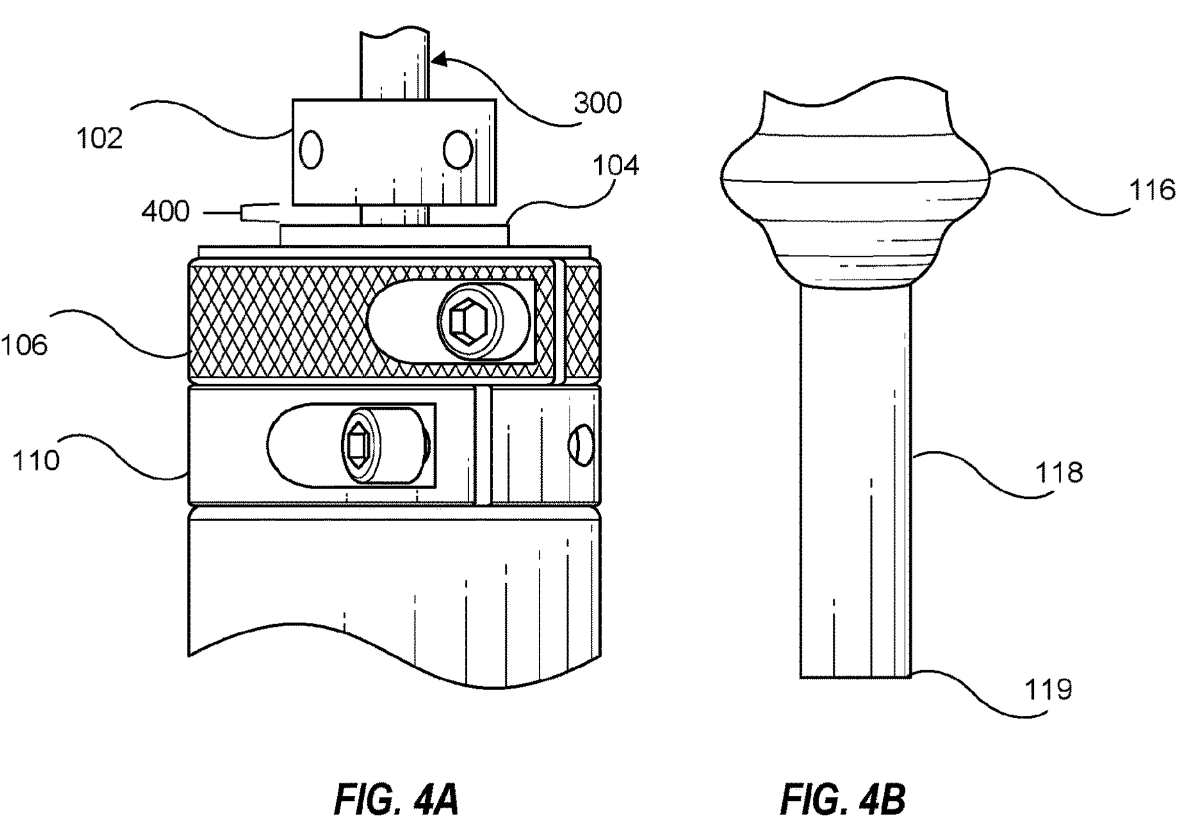
FIG. 4A
FIG. 4B
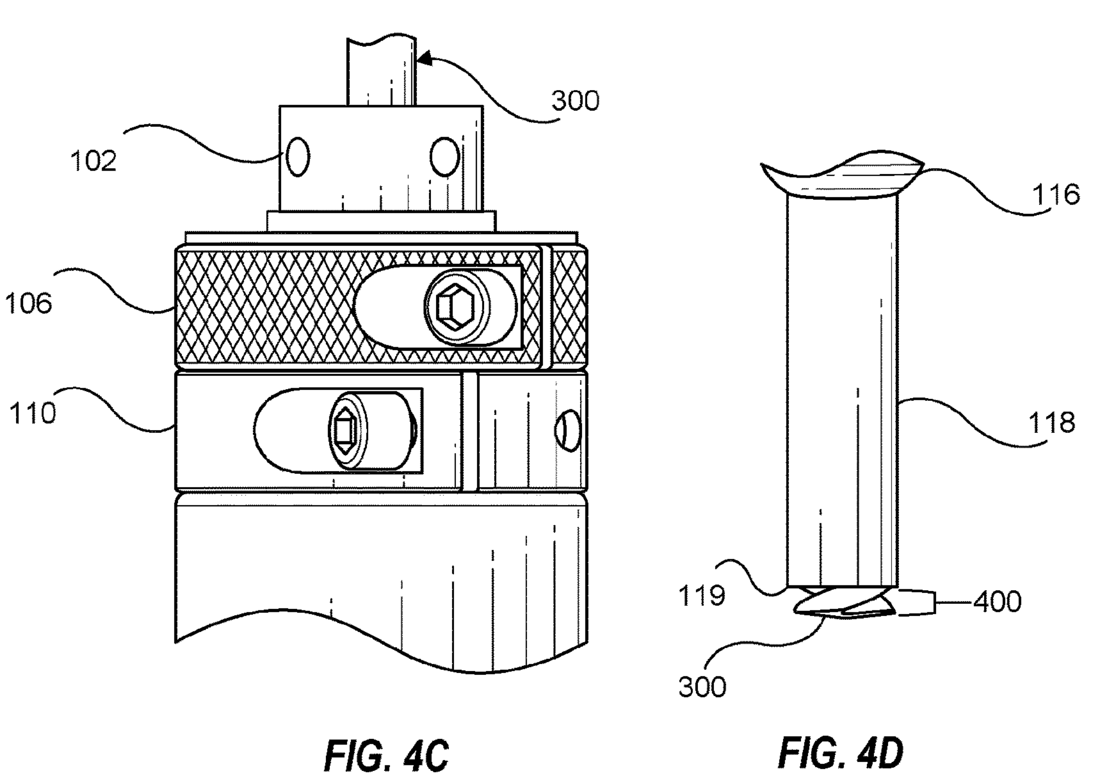
FIG. 4C
FIG. 4D

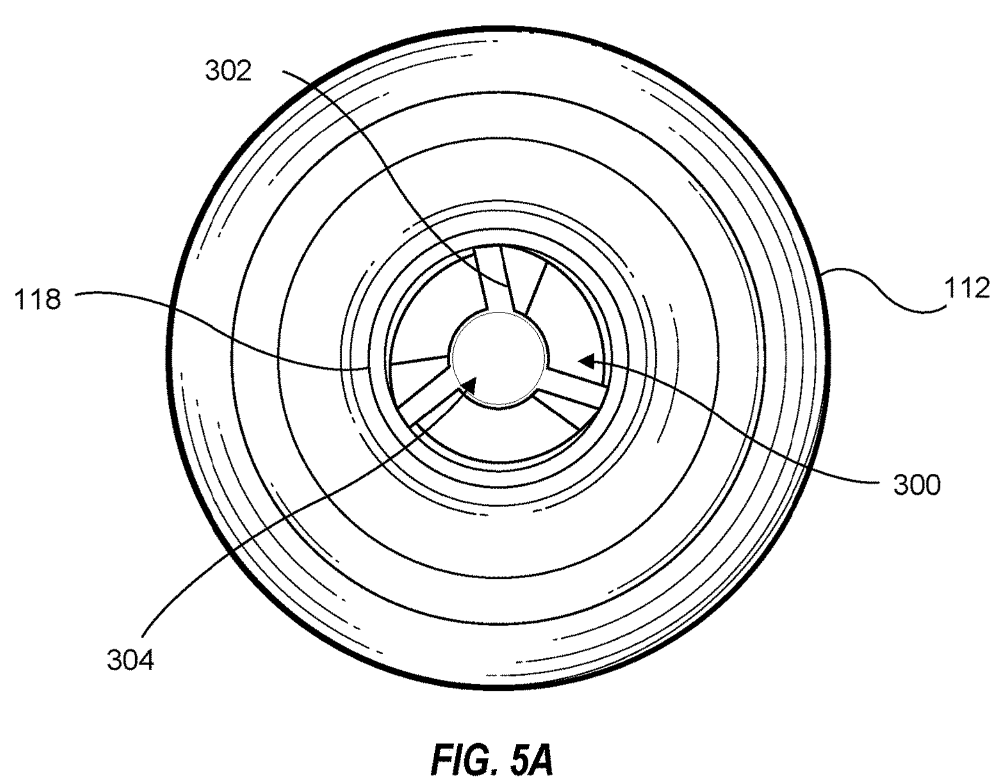
FIG. 5A
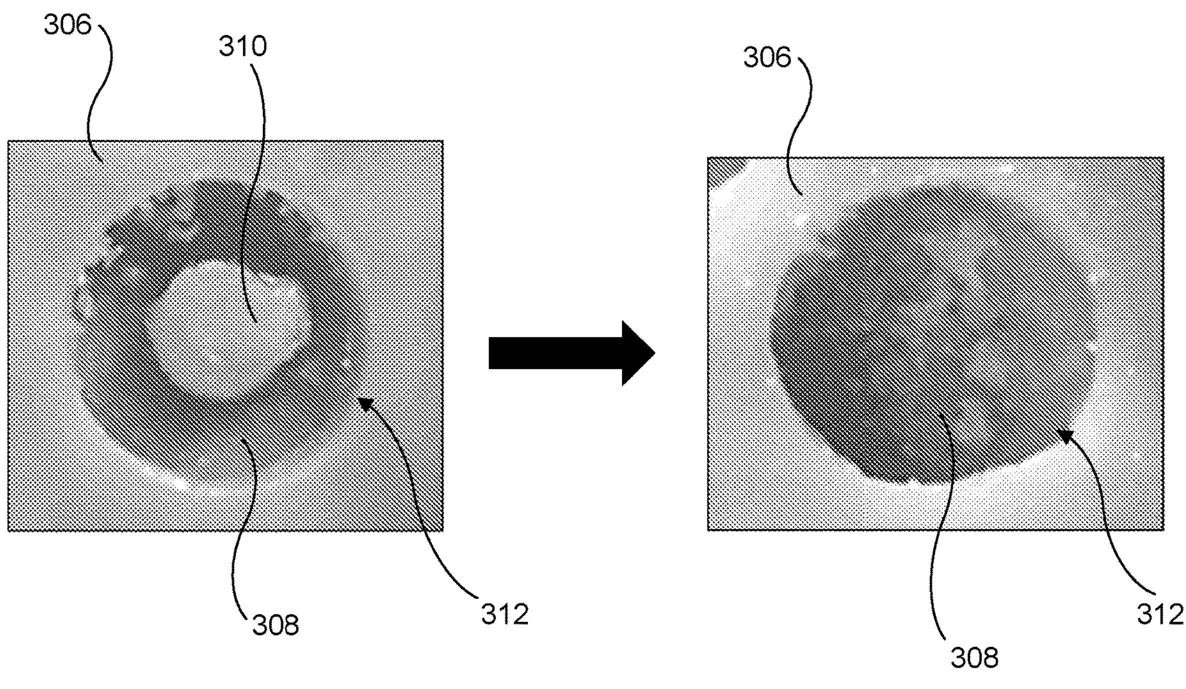
FIG. 5B
FIG. 5C 102
106
110
104
112
602
604
118

102
104
110
112
118
106
100
119

700
702
705
704
708A
708B
707
706A
706B 306
700
312
308

306
708
700
312
308

SYSTEMS, KITS, AND DEVICES FOR DRILLING ARTICULAR CARTILAGE AND METHODS THEREOF

CROSS REFERENCE TO RELATED APPLICATIONS

This Application is an U.S. National Phase of International Patent Application No. PCT/US2021/026564 titled SYSTEMS, KITS, AND DEVICES FOR DRILLING ARTICULAR CARTILAGE AND METHODS THEREOF filed on 9 Apr. 2021, which claims priority to U.S. Provisional Patent Application No. 63/009,576 titled DRILLING SYSTEM AND METHOD filed on 14 Apr. 2020, each of which is hereby incorporated by reference in its entirety as if fully set forth below.

STATEMENT REGARDING FEDERALLY SPONSORED RESEARCH

This invention was made with government support under W81XWH-18-C-0087 awarded by the Department of Defense. The government has certain rights in the invention.

BACKGROUND

Cartilage injuries affect approximately one million Americans annually, resulting in more than 500K cartilage-related procedures. Current methods of treating cartilage injuries include debridement and microfracture, marrow stimulation, autologous chondrocyte implantation (ACI), matrix-induced autologous chondrocyte implantation (MACI), mosaicplasty, osteochondral autografting, and osteochondral allografting. There are at least 350,000 knee arthroplasties performed each year, with chondral lesions present in more than 60% of cases. The number of such procedures is forecasted to increase due to population growth, longevity, and advances in clinical diagnosis.

Autograft and allograft transplantations have been used to treat cartilage injuries. Autograft has been shown to be effective in lesions up to 3.0 cm in diameter, with good-to-excellent outcomes reported even among athletes. Allograft osteochondral transplantation has previously been utilized in combat soldiers, allowing them to return to their military position. However, allograft osteochondral transplantation has proven to be less successful in active duty military populations when compared to civilians. A retrospective review analyzed the effectiveness of allograft osteochondral transplantation in the knee in the active duty population, focusing on the ability of patients to return to their status following the procedure. Although this method of surgery for large lesions of the knee has a good rate of success among civilian patients, it failed to ensure retention on active duty for injured soldiers, particularly when they occupy a physically demanding military position. Many patients treated by allograft osteochondral transplantation have not been able to remain on active duty in their previous role. There is a need for improved transplantation therapies for military populations as well as others who lead a comparably physically active lifestyle, such as professional and amateur athletes, firefighters, and police officers.

Current approaches to osteochondral transplantations to achieve drilling depth in patients is empirical, where the user alternates the use of drilling and measuring guide(s) until a desired drilling depth is reached. In fact, surgeons commonly drill a defect to a depth based on tick marks on a drill bit and then measure that depth with a measuring guide. Unfortunately, such an approach has about a 1 mm tolerance. As a result, this approach is commonly applicable for drilling deep defects with depth greater than 5-6 mm where the error can be tolerated within or about 1 mm. Yet, this approach presents more challenges for creating shallow defects or deep defects that require higher resolution and accuracy in measuring and monitoring the drilling distance. In view of the above, there is a need to resolve these and other problems with the art.

SUMMARY

Described herein are improved grafting systems, methods, and one or more tools as shown and described herein, including each and every novel feature or combination of features disclosed herein.

In some examples, a drilling device is disclosed to provide for precise adjustment and control drilling depth to approximately 50 μm resolution. In some examples, the drilling device allows the user to adjust the drilling depth to a desired depth between approximately 1.00-15.00 mm at a precision of approximately 50 μ m. Once set, the device can be attached to a drill to achieve the desired depth.

In some examples, a method or use is disclosed that includes creating defects on tissues such as articular knee cartilage with controlled depth for implantation of osteochondral grafts or other medical devices In some examples, the herein disclosed system allows an operator to preset a drilling depth to approximately 50 μm (e.g., 10.50 mm, 10.55 mm, 10.60 mm, 10.65 mm, 10.70 mm, and/or the like) resolution before drilling. During drilling, the herein disclosed drilling device is configured to stop drill bit penetration at the preset drilling depth. In some examples, with this system, the implantation process can be more precise than prior approaches and the more desired outcome of having precise surface match can be reached.

In some examples, the herein disclosed system is configured to precisely preset and control the drilling depth.

In some examples, the present disclosure provides a system to remove portions of articular cartilage. The system can include a handle device. The handle device an include a handle, an adjustable shaft collar rotatable to adjust a drill set distance between the adjustable shaft collar and the handle, and a distal drill guide extending from the handle at an end opposite the adjustable shaft collar. The system can include a drill collar attachable to a drill bit and configured to remain stationary along a length of the drill bit once attached. The system can include a rotatable disk positionable between the adjustable shaft collar and the drill collar. The rotatable disk can include a central hole sized to accept the drill bit.

The system can further include the drill bit. A diameter of the drill bit can range from approximately 3.0 mm to approximately 40.0 mm. A diameter of the drill bit can range from approximately 3.0 mm to approximately 10.0 mm. A diameter of the drill bit can be at least approximately 3.0 mm. A diameter of the drill bit, in some examples, may be no greater than approximately 40 mm.

The rotatable disk can include a plurality of bearings. The rotatable disk can be a thrust bearing or an axial needle roller disk. The bearings can be arranged radially around a circumference of the rotatable disk.

The drill collar can include a collar set screw that abuts the drill bit to attach the drill collar thereto.

The handle can include a handle grasping indentation shaped to correspond to a location of a thumb of a user. The handle can include a handle distal flange comprising a finger stop for the user.

The handle comprises a proximal radial flange and a distal radial flange comprising one or more locations for grasping the handle.

The distal drill guide can include a stabilization ring positioned at a distal end of the distal drill guide. The stabilization ring can include a first outer diameter less than a second outer diameter of the distal drill guide proximal to the stabilization ring. The stabilization ring can insert into articular cartilage to provide lateral stability for the distal drill guide.

The distal drill guide can include a taper, such that a first diameter of the distal drill guide proximate the handle is greater than a second diameter of the distal drill guide at a distal tip of the distal drill guide. The taper can be approximately 1 to 15° and approximately 1 to 5 cm long.

The distal drill guide can include one or more apertures extending through an outer wall of the distal drill guide. The one or more apertures can be configured to enable tissue and aspiration fluid to exit the distal drill guide as cartilage is being drilled.

The system can include a first measuring guide having a first measuring thickness and a second measuring guide having a second measuring thickness. The first measuring guide and the second measuring guide can both include a distal convex bevel matching a geometry of a defect created by the drill bit. The first measuring guide and the second measuring guide can both include radial grooves configured to remove debris from a defect created by the drill bit as the respective measuring guide is rotated within the defect.

The system can include a double sided measuring guide comprising a first end having a first depth indicator and a second end having a second depth indicator.

A 90-degree turn of the adjustable shaft collar with respect to the handle can be equivalent to an approximately 200 μm change in the drill set distance.

The adjustable shaft collar can be configured to adjust the drill set distance from between 0.00 mm and 20.00 mm. The adjustable shaft collar can be configured to adjust the drill set distance from between 20.00 mm and 0.00 mm.

In some examples, the present disclosure provides one or more kits that include one or more of the components of the system described above. In some examples, the present disclosure provides a method of drilling a circular cavity in articular cartilage using the system described above.

In some examples, the present disclosure provides a method of preparing articular cartilage for receiving a graft tissue. The method can include connecting a drill collar to a drill bit.

The method can include inserting a distal end of the drill bit into an adjustable shaft collar of a handle device. The method can include advancing the distal end of the drill bit through an internal cannulation of the handle device until the distal end of the drill bit is proximate a distal tip of a distal drill guide of the handle device and the drill collar abuts a rotatable disk disposed between the drill collar and the adjustable shaft collar. The method can include rotating the adjustable shaft collar to cause the adjustable shaft collar to move axially with respect to a handle of the handle device until the distal end of the drill bit extends from the distal drill guide a desired drill depth.

The method can include retracting the drill bit from the internal cannulation such that the distal end of the drill bit does not extend from a distal tip of the distal drill guide. The method can include placing the distal tip of the distal drill guide perpendicular to a surface to be drilled. The method can include advancing the drill bit through the internal cannulation of the handle device until the drill collar contacts the adjustable shaft collar.

The surface can be articular cartilage. The distal end of the drill bit can be advanced proximate to subchondral bone.

The method can include removing a cannulation remnant from a circular defect created by the drill bit using a bone nipper or biopsy punch, wherein the drill bit is cannulated.

The method can include removing the drill bit and handle device from the surface. The method can include inserting a first measuring guide into a circular defect created by the drill bit. The method can include measuring a depth of the circular defect using a first tip of the first measuring guide.

The method can include removing the first measuring guide from the circular defect. The method can include inserting a second measuring guide into the circular defect. The method can include measuring the depth of the circular defect using a second tip of the second measuring guide.

The method can include rotating the first measuring guide to remove tissue within the circular defect with radial grooves disposed on the first tip of the first measuring guide.

The first tip of the first measuring guide can include a convex bevel to match the circular defect.

The method can include removing the drill bit and handle device from the surface. The method can include inserting a first end of a double sided measuring guide into a circular defect created by the drill bit, the first end having a first measuring height. The method can include measuring a depth of the circular defect using the first end of the double sided measuring guide.

The method can include removing the double sided measuring guide from the circular defect. The method can include rotating the double sided measuring guide end for end. The method can include inserting a second end of the double sided measuring guide into the circular defect, the second end having a second measuring height different than the first measuring height. The method can include measuring the depth of the circular defect using the second end of the double sided measuring guide.

The first end of the double sided measuring can include a first depth indicator. The second end of the double sided measuring can include a second depth indicator.

The method can include retracting the drill bit from the internal cannulation such that the distal end of the drill bit does not extend from a distal tip of the distal drill guide. The method can include placing a stabilization ring of the distal tip of the distal drill guide perpendicular to articular cartilage and proximate a chondral defect. The method can include advancing the handle device until the stabilization ring is at least partially embedded within the articular cartilage.

The method can include removing tissue debris from a distal drill guide aperture disposed in an outer surface of the distal drill guide.

In some examples, the present disclosure provides a kit for removing portions of articular cartilage. The kit can include a handle device. The handle device can include a handle, an adjustable shaft collar rotatable to adjust a drill set distance between the adjustable shaft collar and the handle, and a distal drill guide extending from the handle at an end opposite the adjustable shaft collar. The kit can include a drill bit. The kit can include a drill collar attachable to the drill bit. The kit can include a rotatable disk positionable between the adjustable shaft collar and the drill collar. The rotatable disk including a central hole sized to accept the drill bit. The kit can include a first measuring guide configured to measure a depth of a circular defect created by the drill bit.

The kit can include a second measuring guide, wherein the first measuring guide has a first measuring thickness and the second measuring guide has a second measuring thickness different than the first measuring thickness. The first measuring guide and the second measuring guide can both have a distal convex bevel matching a geometry of a defect created by the drill bit. The first measuring guide and the second measuring guide can both include radial grooves configured to remove debris from a defect created by the drill bit as the respective measuring guide is rotated within the defect.

The first measuring guide can be a double sided measuring guide comprising a first end having a first depth indicator and a second end having a second depth indicator.

To the accomplishment of the foregoing and related ends, certain illustrative aspects are described herein in connection with the following description and the appended drawings. These aspects are indicative, however, of but a few of the various ways in which the principles of the claimed subject matter may be employed and the claimed subject matter is intended to include all such aspects and their equivalents. Other advantages and novel features may become apparent from the following detailed description when considered in conjunction with the drawings.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

FIGS. 4A and 4B depicts a close-up view of the example drilling device of FIGS. 1A and 1B before drilling.

FIGS. 4C and 4D depicts a close-up view of the example drilling device of FIGS. 1A and 1B at the end of drilling.

FIG. 5A depicts a close-up view of an example drill bit tightly fitted into a handle device.

FIG. 5B depicts a close-up view of an example defect, immediately following drilling.

FIG. 5C depicts a close-up view of an example defect after a cannulation remnant within the articular cartilage piece is removed.

DETAILED DESCRIPTION

Figure 1A:
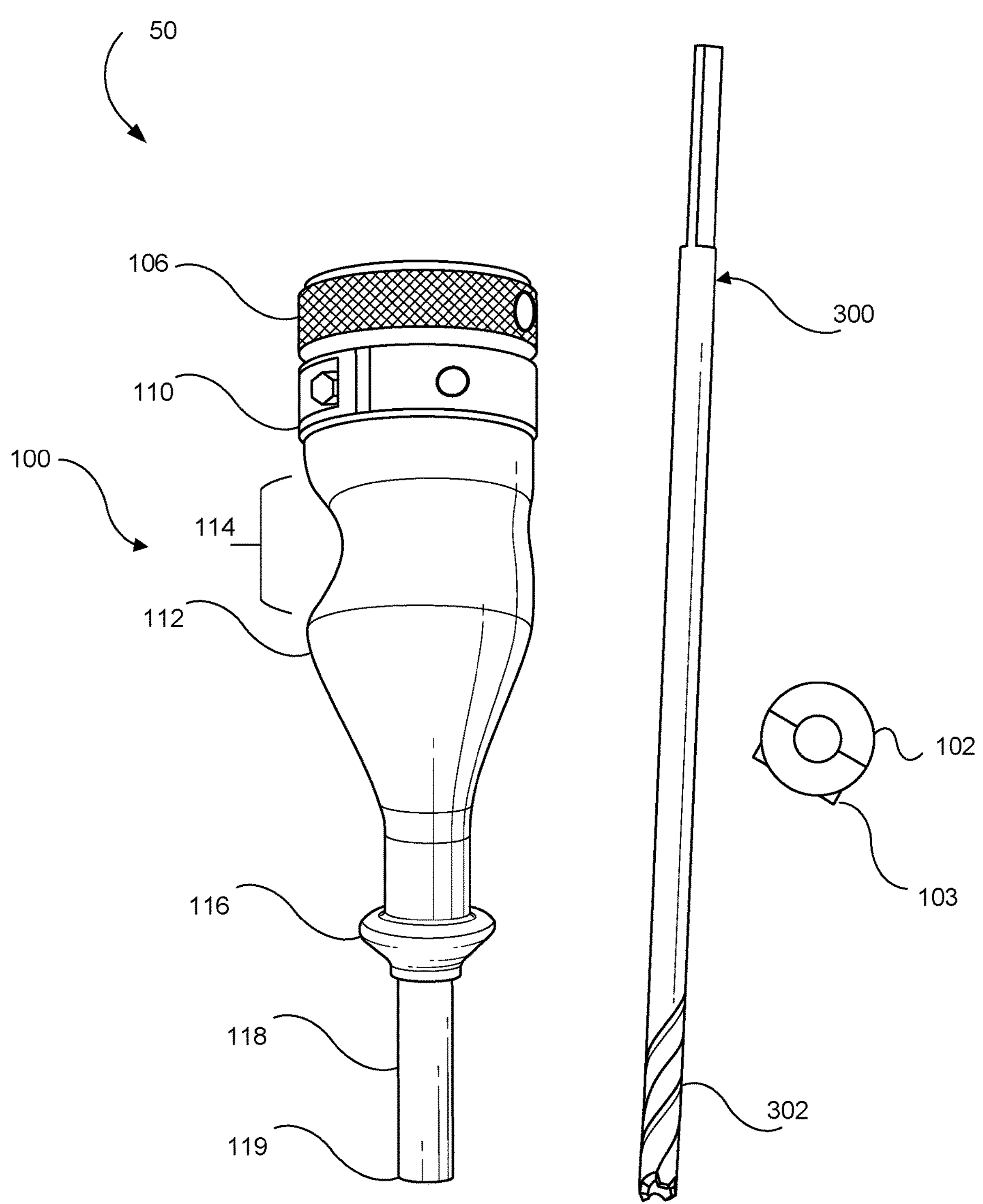
FIG. 1A depicts an example unassembled drilling system of this disclosure.

Although example embodiments of the disclosed technology are explained in detail herein, it is to be understood that other embodiments are contemplated. Accordingly, it is not intended that the disclosed technology be limited in its scope to the details of construction and arrangement of components set forth in the following description or illustrated in the drawings. For example, while certain drilling devices of this disclosure may be shown with certain diameters (e.g., 6 mm), it is contemplated that the drilling devices and related instrumentalities can be made with other diameters greater than or less than those described herein (e.g., diameters including but not limited to less than 6 mm, approximately 10.0 mm, 20.0 mm, 30.0 mm, 40.0 mm, etc.). The disclosed technology is capable of other embodiments and of being practiced or carried out in various ways.

As used in the specification and the appended claims, the singular forms "a," "an" and "the" include plural referents unless the context clearly dictates otherwise. By "comprising" or "containing" or "including" it is meant that at least the named compound, element, particle, or method step is present in the composition or article or method, but does not exclude the presence of other compounds, materials, particles, method steps, even if the other such compounds, material, particles, method steps have the same function as what is named.

As used herein, the terms "about" or "approximately" for any numerical values or ranges indicate a suitable dimensional tolerance that allows the part or collection of components to function for its intended purpose as described herein. More specifically, "about" or "approximately" can refer to the range of values±20% of the recited value, e.g. "about 90%" can refer to the range of values from 71% to 99%.

As discussed herein, "operator" can include a doctor, surgeon, or any other individual or delivery instrumentation associated with use or operation of the system and instrumentalities of this disclosure.

As discussed herein, a "patient," "host," "user," and "subject" can be a human or any animal. It should be appreciated that an animal can be a variety of any applicable type, including, but not limited thereto, mammal, veterinarian animal, livestock animal or pet type animal, etc. As an example, the animal can be a laboratory animal specifically selected to have certain characteristics similar to a human (e.g., rat, dog, pig, monkey, or the like). It should be appreciated that the subject can be any applicable human patient, for example.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the disclosed technology. Similarly, it is also to be understood that the mention of one or more components in a device or system does not preclude the presence of additional components or intervening components between those components expressly identified.

In some examples, a method or use is disclosed that includes creating defects on tissues such as articular knee cartilage with controlled depth for implantation of osteochondral grafts, tissue grafts, or other medical devices. The system (e.g., system 50 described below), which can include a handle device 100, a collar (e.g., drill collar 102), and a drill bit (e.g., drill bit 300) shown in FIGS. 1A (unassembled) and 1B (assembled), is particularly configured to create shallow defects, which can require geometric and dimensional precision and can include corresponding technical challenges, as opposed to creating larger defects in a target site. System 50 can be configured to allow relatively precise adjustment to control the drilling depth (e.g., to approximately 50 μm resolution) to create defects on tissues such as articular knee cartilage with controlled depth for implantation of osteochondral grafts/tissue filler or other medical devices. System 50 can be configured to allow the operator to adjust the drilling depth to a desired depth between approximately 1.00-15.00 mm at a precision of approximately 50 μm changes to drilling depth. Once set, system 50 can be used with a drill and bit (e.g., drill bit 300) to achieve the pre-defined drill depth.

To facilitate and simplify the surgical process, the handle device 100 can be assembled and pre-set at a desired drilling depth offsite and away from the surgical site before shipping it to the destination for clinical use. However, handle device 100 is not so limited and can be assembled or manufactured differently as needed or required, for example on a back table in an operating room setting. Pre-setting the drilling depth can ensure consistency and accuracy of the drilling depth.

Figure 1B:
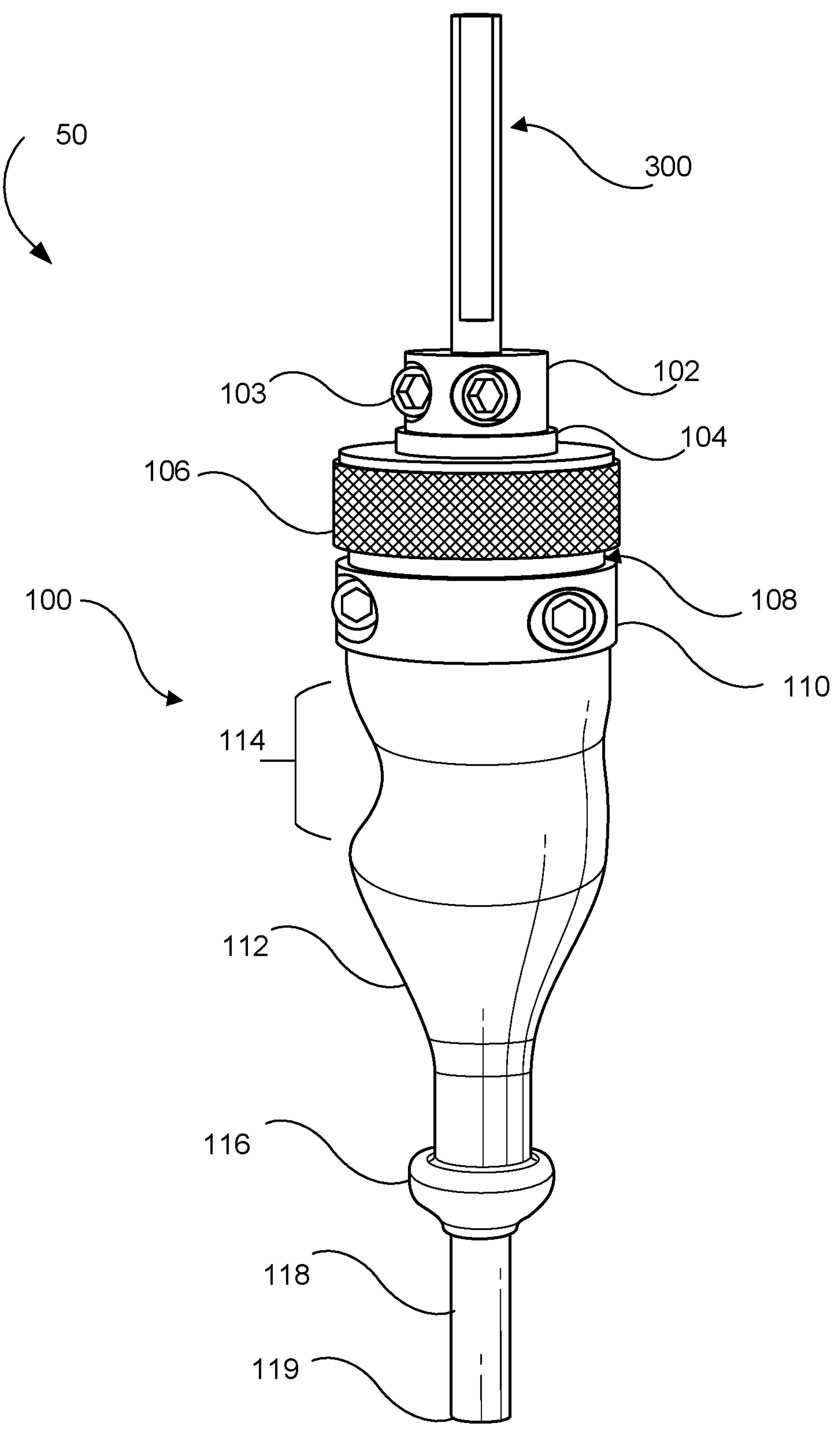
FIG. 1B depicts another view of the assembled example drilling system of FIG. 1A.
Figure 3A:
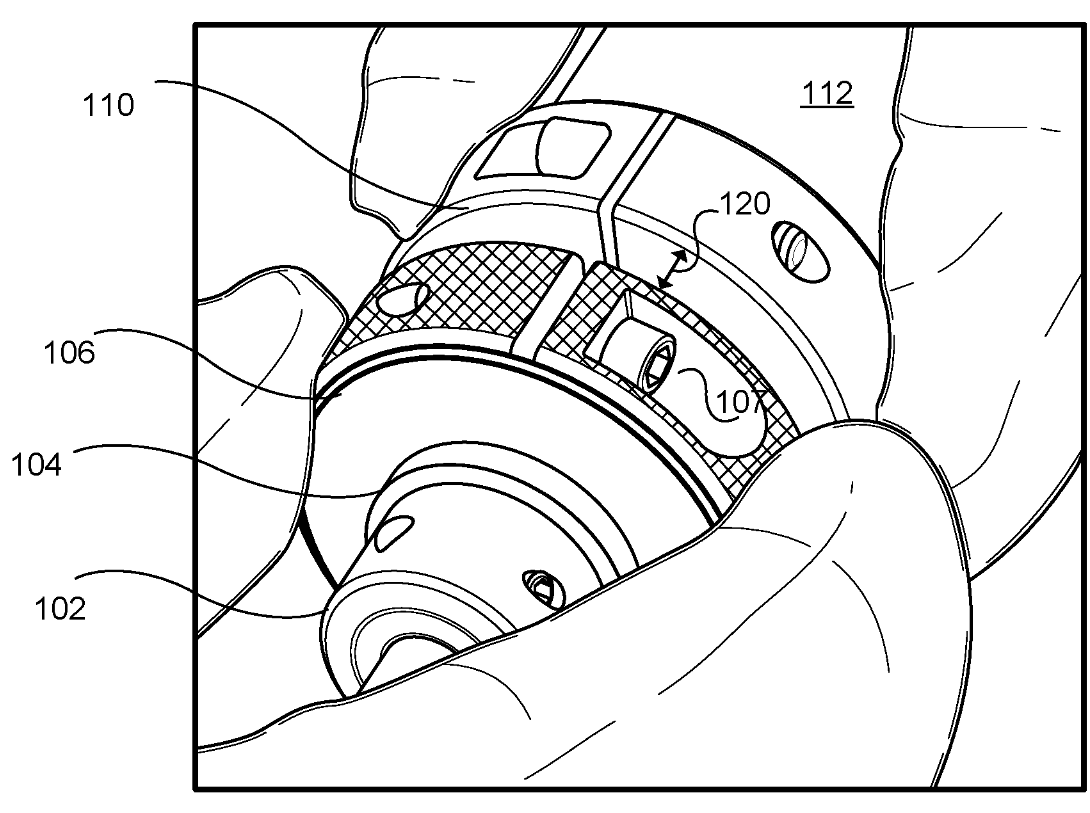
FIGS. 3A and 3B depict close-up, side perspective views of the example drilling device of FIGS. 1A and 1B.
Figure 3B:
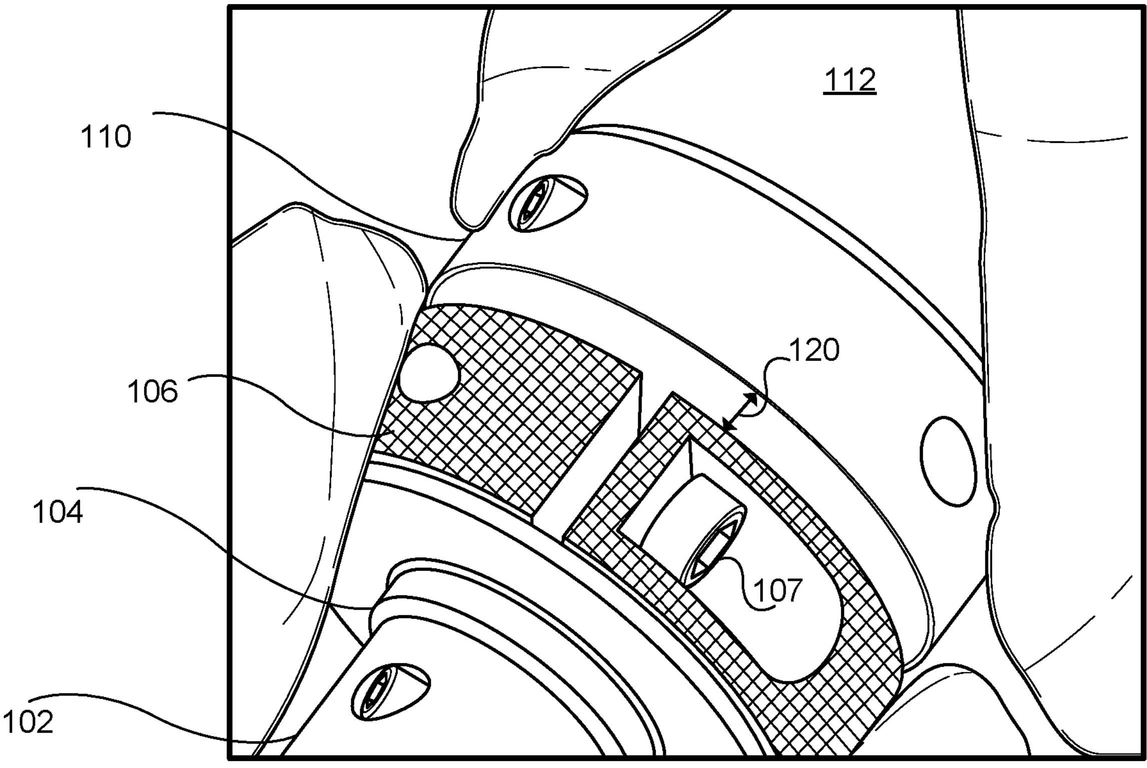

Referring to FIGS. 1A and 1B, the system 50 can include a handle device 100 and a drill collar 102 configured to fit upon a drill bit 300. The drill collar 102 can include a collar set screw 103 that can be tightened to affix or attach the drill collar 102 to the drill bit 300. The handle device 100 can include an adjustable shaft collar 106 and a fixed ring 110 proximate a handle 112 of the handle device 100. The adjustable shaft collar 106 can be rotated with respect to the fixed ring 110 so as to adjust a drilling depth for the threads 302 of the drill bit 300. For example, external threads can be placed either on the adjustable shaft collar 106 or the fixed ring 110 that can engage with internal threads on the other of the adjustable shaft collar 106 or the fixed ring 110 so that, as the adjustable shaft collar 106 is rotated, a set drill distance 120 (as shown in FIGS. 3A and 3B) can be adjusted. Further, the adjustable shaft collar 106 can include an adjustable shaft set screw 107 that can be adjusted to set the amount of resistance provided to the adjustable collar shaft 106 as the collar shaft is rotated. For example, adjustable shaft set screw 107 can abut and press upon the external threads between the adjustable shaft collar 106 and the fixed ring 110. Referring again to the adjustable shaft collar 106, rotating the collar enables fine adjustments to the drilling depth. If the defect is not deep enough (e.g., shallow), the dial can be used to add a small incremental distance (where every 90-degree turn can be equivalent to ~200 μm) to achieve desired defect depth such as 1.50 mm, 2.0 mm, etc.

Referring to assembled system 50 in FIG. 1A, the handle device 100 can include ergonomic features to help facilitate precise placement of a distal drill guide 118 at a defect site. As described above, an aspect of the present disclosure includes the ability to drill precise location with high-resolution drilling accuracy. The shape of the handle 112 can also be customized so as to facility precise placement at the defect site. The handle 112 can include a handle grasping indentation 114 asymmetrically positioned on only one side, multiple sides, or symmetrically arranged on all sides thereof. In one example, indentation 114 can be sized and shaped to correspond to the web between the user's thumb and forefinger. The handle 112 can include a handle distal flange 116 positioned proximate the distal drill guide 118 of the handle device 100. The handle distal flange 116 can provide a point at which the user's forefinger and thumb can rest upon to position the distal flange 116.

Figure 2:
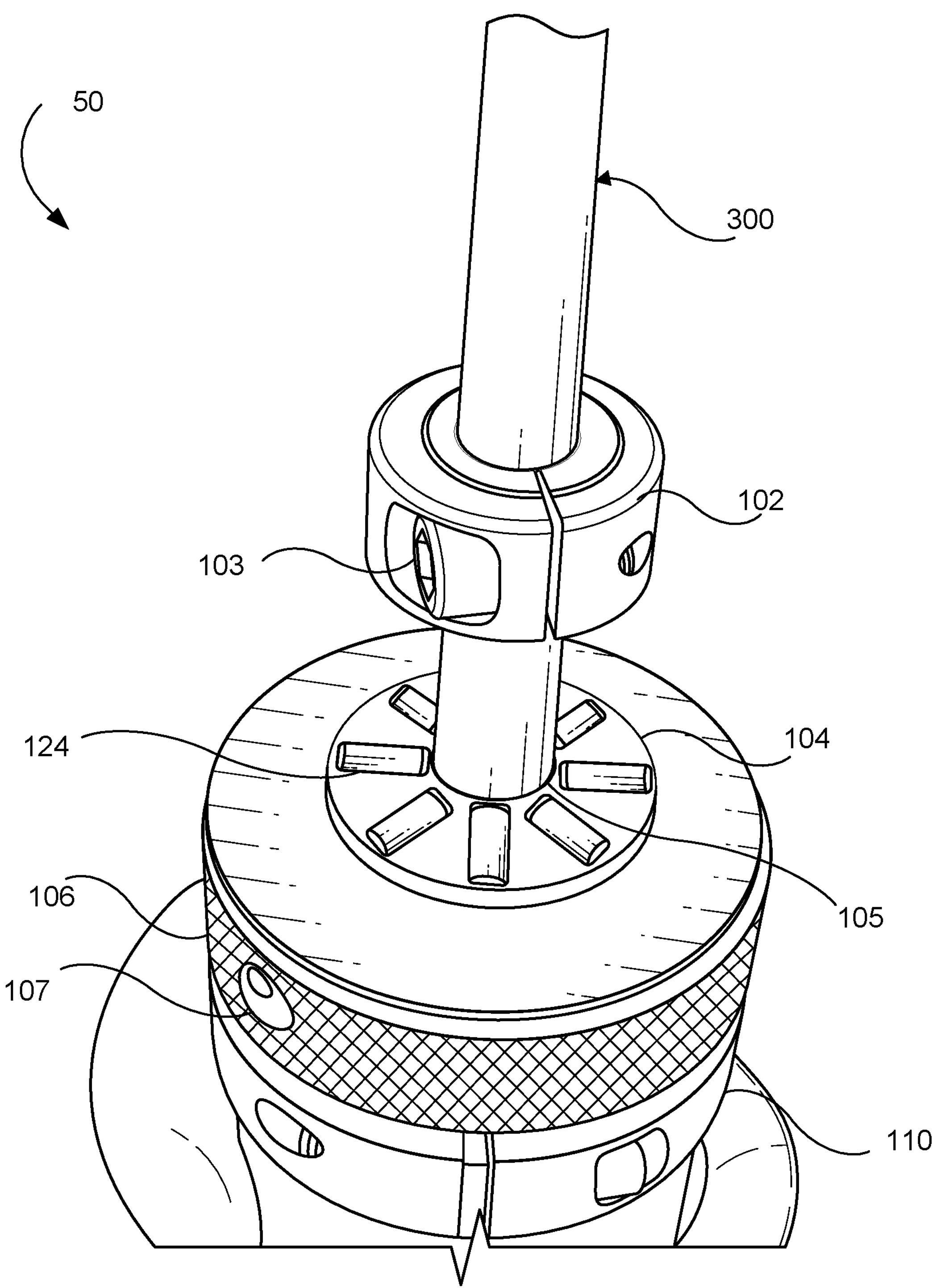
FIG. 2 depicts a close-up, upper perspective view of the example drilling device of FIGS. 1A and 1B.

Turning to FIG. 2, a close-up, upper perspective view of an assembled system 50 is shown. The drill collar 102 can be tightly fitted onto the body of drill bit 300. Drill collar 102 can contact a spinning disk 104 when the drilling distance is achieved. The disk 104 can be positioned between the adjustable shaft collar 106 and the drill collar 102 when the system 50 is assembled. The drill bit 300 can fit within a central hole 105 of the disk 104. The disk 104 can be configured to spin when drill collar 102 contacts disk 104, thereby indicating an end of the drilling process. Although it is contemplated that the drill collar 102 can merely contact the adjustable shaft collar 106 when the drilling process is completed, the disk 104 provides an additional degree of rotational stability for the system 50. For example, when the drill collar 102 contacts the disk 104, the disk 104 can spin freely and thereby shield the handle 112 from receiving the torsional force of the drill bit 300. The drill bit 300 can have a diameter that ranges from approximately 3.0 mm to approximately 40.0 mm. For example, the diameter of the drill bit can range from approximately 3.0 mm to approximately 10.0 mm, or at least approximately 3.0 mm.

Further, in some examples, since the adjustable shaft collar 106 is configured to rotate with respect to the fixed ring 110, the disk 104 can prevent the adjustable shaft collar 106 from rotating with the drill collar 102, thereby preventing inadvertent changes to the set drill distance 120. The disk 104 can be a solid disk that spins with the drill collar 102, and the solid disk can comprise a metallic material, plastic material to provide decreased friction, and the like. In some embodiments, the disk 104 can include bearings 124 to facilitate rotation with the spinning drill collar 102. The bearings 124 can be spherical bearings, rotating bars (as shown), and the like, yet, other bearing 124 shapes and configurations are contemplated. For example, FIG. 2 shows an example disk 104 that is an axial needle roller disk and the bearings 124 are arranged radially around a circumference of the rotatable disk 104. Another example would disk 104 can include thrust bearing.

The system 50 can include other components for osteochondral defect creation, including but without limitation, the handle device 100 which guides the drilling and controls the drilling depth, the drill bit 300 and/or drill collar 102, and measuring guides (e.g., guide 200 and/or double sided measuring guide 700 of this disclosure), which can measure and confirm the depth of the defect. Handle device 100 can be configured to limit the drilling depth to, in some examples, approximately 1.50-20.00 mm. However, other drilling depths are contemplated that can be outside this approximate range. In some examples, the drilling depth can be pre-adjusted and tuned via adjustable shaft collar 106, and/or by adjusting a position the drill collar 102 along a length of the drill bit 300.

FIGS. 3A and 3B depicts a close-up, side perspective views of a handle device 100 showing an operator adjusting the adjustable shaft collar 106 to set a drilling depth (e.g., drill depth 400 shown in FIG. 4D below). In this method, drill collar 102 can be locked onto the drill bit 300 where the adjustable shaft collar 106 starts off at 0° position (FIG. 3A) and the tip of the drill bit 300 is level with the tip of the shaft of device 100, as shown in FIG. 4B for example. In some examples, the adjustable shaft collar 106 can be rotated to adjust the drilling distance. For example, the adjustable shaft collar 106 can be turned a certain degree to adjust a set drill distance 120 (e.g., a distance between the adjustable shaft collar 106 and the fixed ring 110 on the handle 112), which, since the drill collar 102 is fixed on the drill bit 300, adjusts the distance the distal tip of the drill bit 300 will extend from the distal tip 119 of the distal drill guide 118. To illustrate using a non-limiting example, the adjustable shaft collar 106 can be rotated approximately 675° (e.g., approximately 1 full rotation and ⅞ rotation) (FIG. 3B) to create a distance of approximately 1.50 mm between drill collar 102 and the disk 104 to correspondingly result in a penetration depth of approximately 1.50 mm.

FIGS. 4A-4D depict close-up views of the example drilling device before drilling and at the end of drilling. In particular, FIG. 4A depicts a drilling distance pre-set by the adjustable shaft collar 106, leaving a distance between drill collar 102 and disk 104 prior to drilling. To use an example, in FIG. 4A, the drilling distance is shown preset to result in a defect depth of 1.50 mm, which can correspond to a typical drilling depth for drilling articular cartilage. In FIG. 4A, the adjustable shaft collar 106 is dialed down to the preferred drill depth. At this point, the distal threads 302 of the drill bit 300 can be flush with a distal tip 119 of the distal drill guide 118. The distance between the disk 104 and the drill collar 102 can be the predetermined drill depth 400. In FIG. 4C, the drilling process is completed, and the drill collar 102 abuts the disk 104. At this point, the distal end (e.g., threads 302) of the drill bit 300 can extend beyond the distal tip 119 of the distal drill guide 118 a distance equal to the drill depth 400. In practice, the drill bit 300 can be attached to a drill (e.g., surgical or hand drill). The distal tip 119 of the distal drill guide 118 can be arranged perpendicular to the cartilage surface prior to drilling. In FIG. 4D, the tip of the drill bit shows a pentation depth of 1.50 mm, which is equivalent to the preset drilling distance.

FIG. 5A depicts a close-up bottom view of an example drill bit 300 fitted inside the handle device 100. FIGS. 5B and 5C depict close-up views of an example cartilage defect. Referring to FIG. 5A, the drill bit 300 can fit within an internal cannulation 122 of the handle device 100 that extends through the adjustable shaft collar 106, the fixed ring 110, the handle 112, and the distal drill guide 118 of the handle device 100. In some examples, the drill bit 300 can include a cannulation 304, since many procedures for drilling cartilage defects include using a guide wire embedded into the subchondral bone 308 and advancing cannulated bit over the drill guide. In these examples, as the threads 302 of the drill bit 300 advance through the articular cartilage 306 and to the subchondral bone 308, a cannulation remnant 310 (e.g., a circle corresponding to the cannulation 304) can be left behind within the circular drill defect 312 created by the drill bit 300, since no guide wire is necessary with the present system 50, though one can be used. In examples without use of a guide wire, the cannulation remnant 310 in the defect can be removed, as shown in FIG. 5C, before the depth of the defect is measured. Prior to measuring the defect, a biopsy punch (e.g., of approximately 3 mm) or bone nipper can be used to remove the center bone piece at the center of the defect. In other examples, if a solid drill bit (e.g., non-cannulated) is used, it is contemplated that there will be no cannulation remnant 310 to be removed.

Figure 6B:
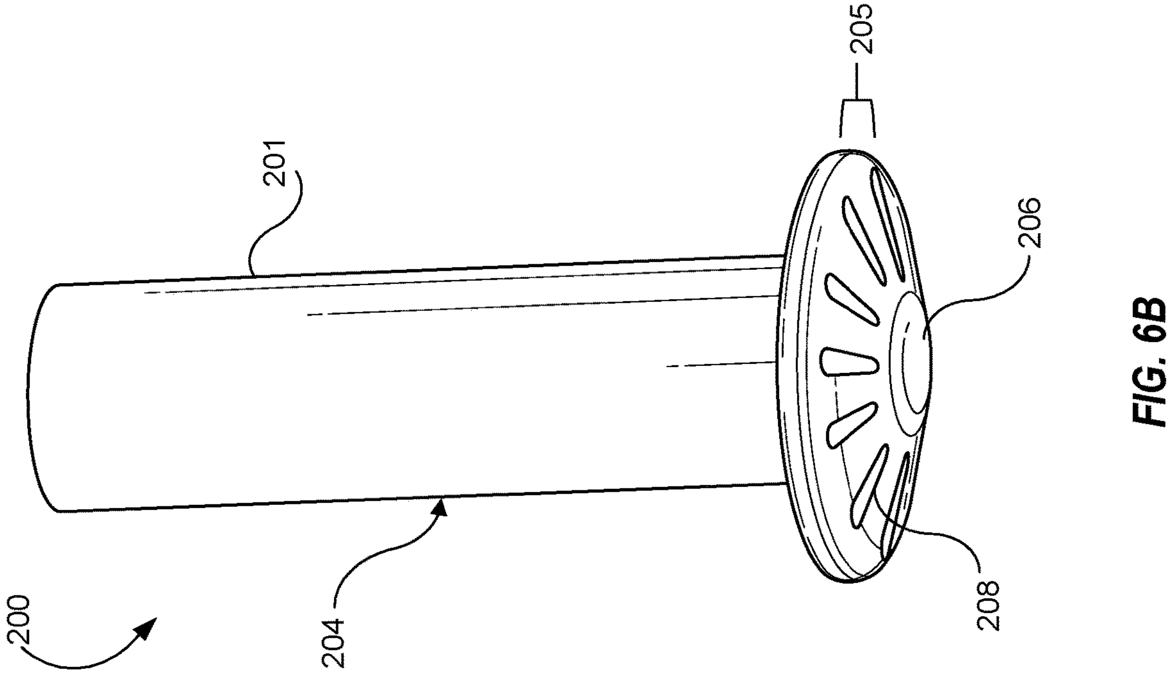
FIG. 6B depicts a close-up of one example measuring guide with a known thickness of 1.5 mm.
Figure 6A:
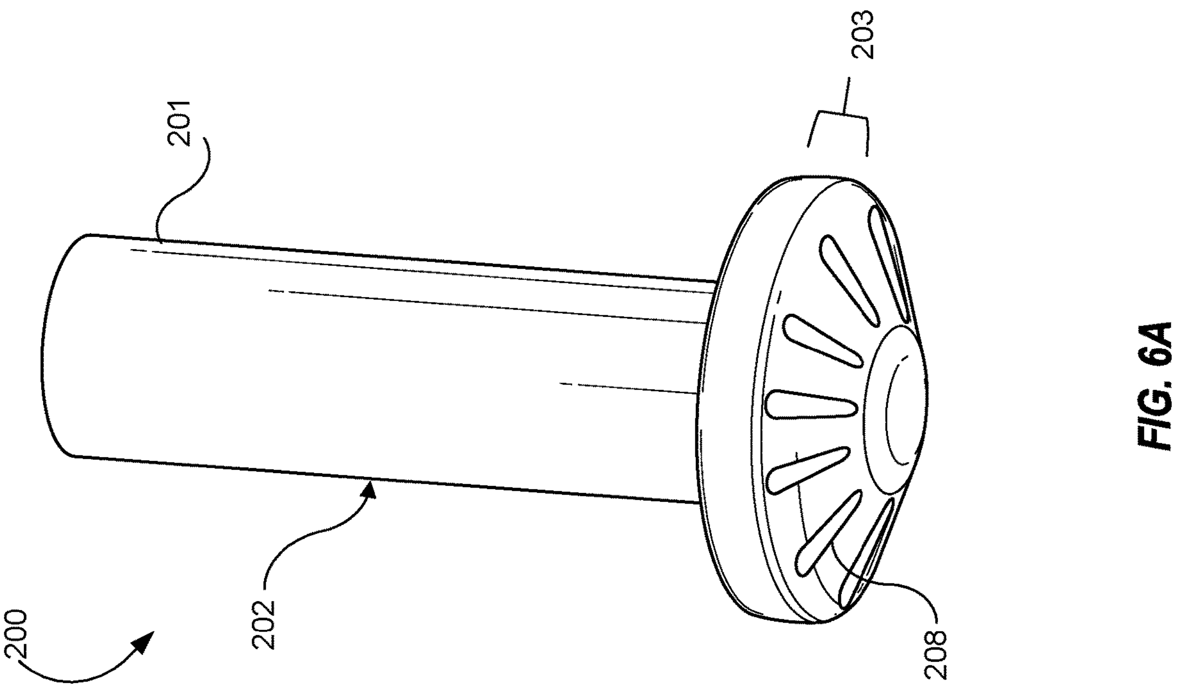
FIG. 6A depicts a close-up of one example measuring guide with a known thickness of 2.0 mm.

FIGS. 6A and 6B depicts a close-up of example measuring guides 200 with different measuring thicknesses. The system 50 (or a kit that includes components of the system 50) can include different measuring guides 200 useable for differing thicknesses of articular cartilage 306. For example, the first measuring guide 202 in FIG. 6A can have a distal tip 206 having a first thickness 203, while a second measuring guide 204 in FIG. 6B can have a distal tip 206 having a second thickness 205. Using an example to illustrate, the first measuring guide 202 in FIG. 6A can have a 2.0 mm first thickness 203, while the second measuring guide 204 in FIG. 6B can have a 1.5 mm second thickness 205. These 2.0 mm and 1.5 mm thickness examples correspond to typical articular cartilage defects but are used only as illustrative examples. The distal tip 206 of the measuring guides 200 can have a convex bevel to match the geometry of the defect created by bit 300. In some examples, distal tip 206 can include grooves 208 extending radially along the surface of the distal tip 206 to facilitate removal of any bone, cartilage, or other tissue debris within the drilled defect. The measuring guides 200 (e.g., first measuring guide 202 and/or second measuring guide 204) can be made of moldable plastics, metals, and/or the like. In some examples, the measuring guides 200 can include radiopaque markers so that they are visible under fluoroscopy if inadvertently dropped into an incision of a patient. It is understood that one or more guides 200 can be included in a deliverable kit that can include the handle device 100, drill collar 102, bit 300 and any other portion of the system 50 described herein.

Figure 7A:
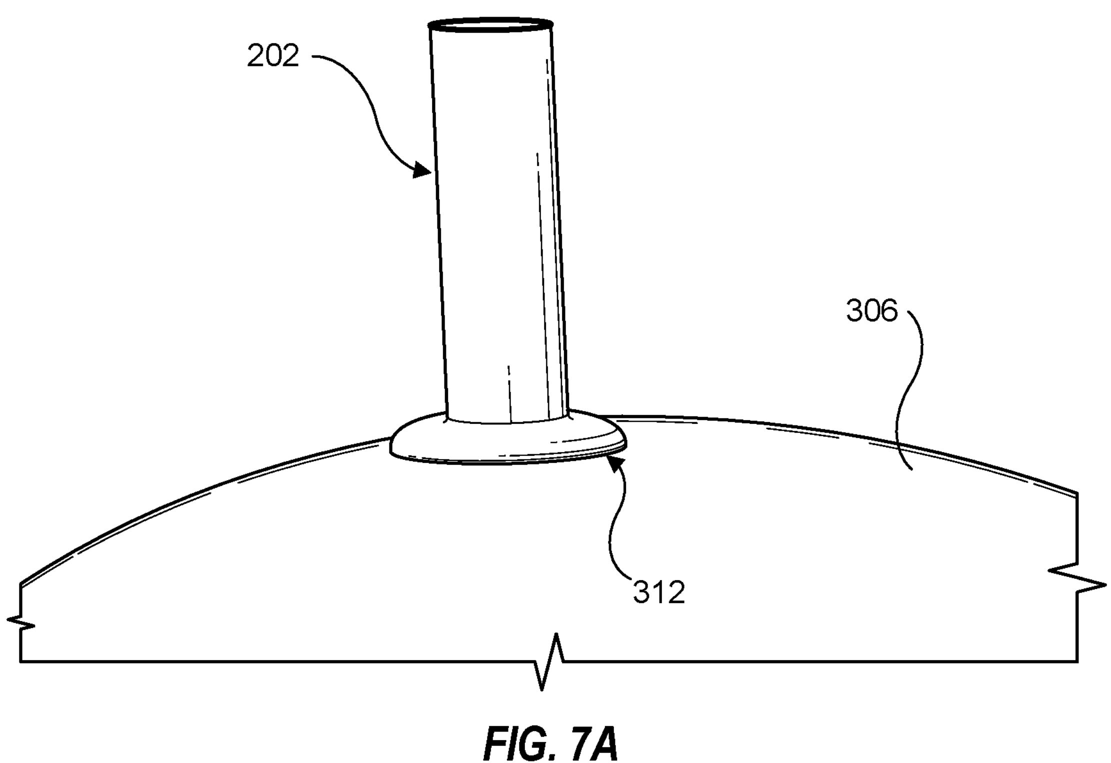
FIG. 7A depicts a close-up of an example guide measuring the defect site.
Figure 7B:
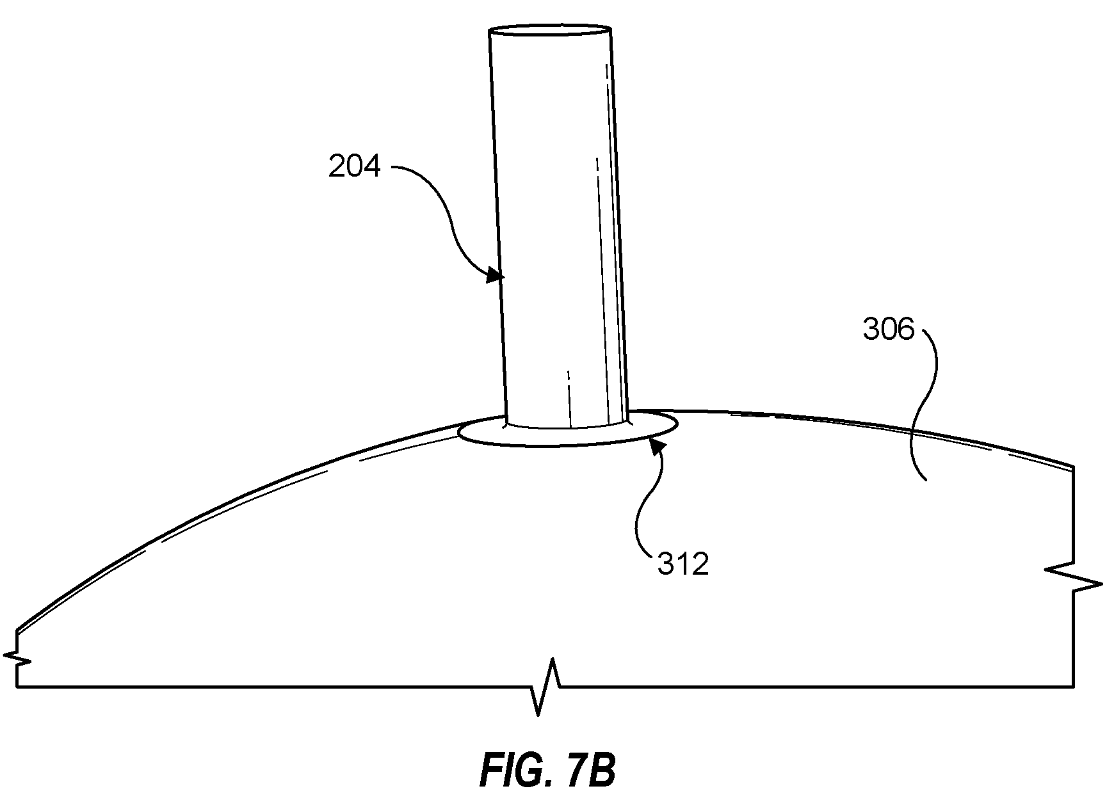
FIG. 7B depicts a close-up of the example guide of FIG. 7A measuring the defect site with a depth closely matching the guide at the defect site.

FIGS. 7A and 7B depict the measuring guides 200 of FIGS. 6A and 6B, and demonstrate how the measuring guides 200 can be used to determine whether the defect depth is below or greater than the known thickness of the guides. Referring to FIG. 7A, the image shows a distal tip 206 that is 2.0 mm in thickness (e.g., the first measuring guide 202 in FIG. 6A) inserted into a defect site with a depth 1.5 mm depth (e.g., as set in FIGS. 4A-4D). As can be seen, a thicker measuring guide can be inserted into the defect to determine if a depth of the defect is within a range between the different thicknesses of the measuring guides. In FIG. 7A, the 2.0 mm measuring guide protrudes slightly from the articular cartilage 306, showing the defect is less than 2.0 mm in depth. Referring to FIG. 7B, the image shows a distal tip 206 that is 1.5 mm in thickness (e.g., the second measuring guide 204 in FIG. 6B) inserted into the same defect. As can be seen, the guide is sitting flush with the defect or recessed slightly within the articular cartilage 306, showing that the defect is approximately 1.5 mm in depth.

Figure 8A:
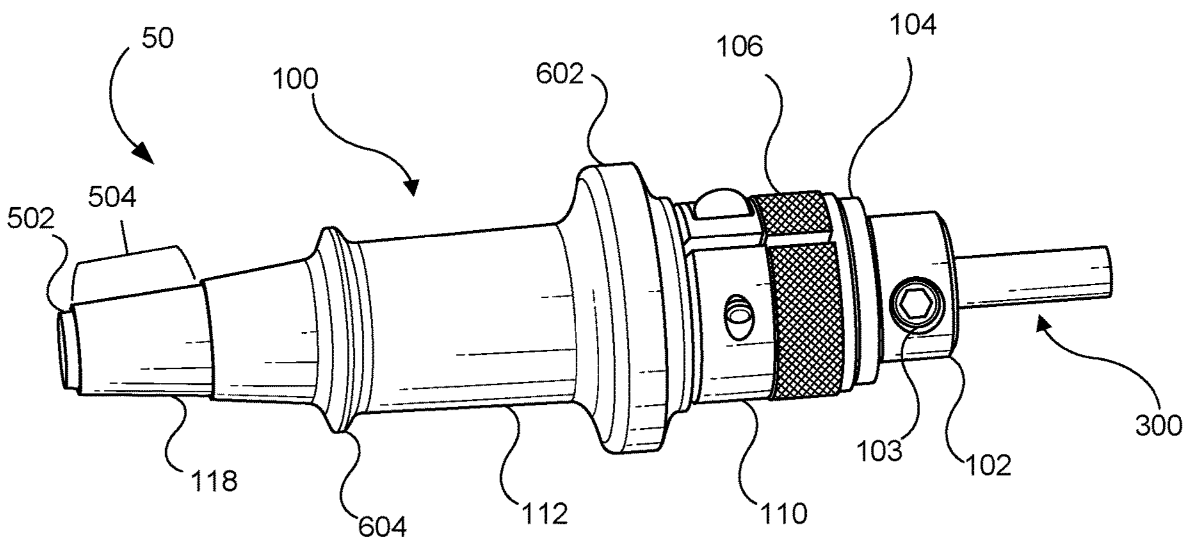
FIG. 8A is an alternative view of an assembled example drilling system.
Figure 8B:
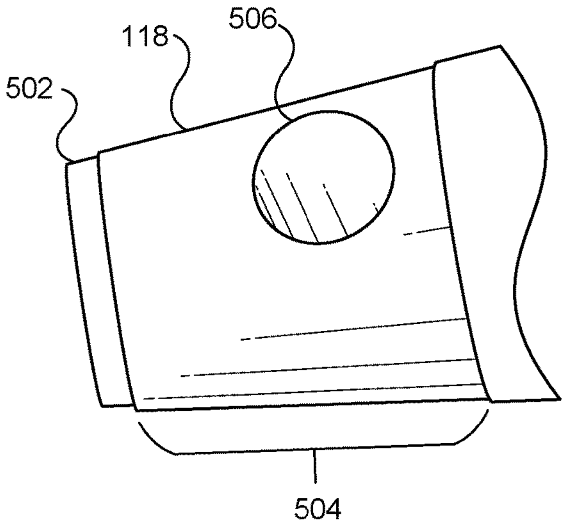
FIG. 8B is a close up view of a distal drill guide of a handle device.

FIG. 8A is an alternative view of an assembled example drilling system 50; and FIG. 8B is a close up view of a distal drill guide 118 of a handle device 100. As described above with reference to FIGS. 1A and 1B, the handle device 100 can include ergonomic features to help facilitate precise placement of a distal drill guide 118 to a defect site. The example handle device 100 in FIG. 8A includes a proximal radial flange 602 and a distal radial flange 604, both of which can facilitate grabbing the handle device 100 at the handle 112 and positioning the distal drill guide 118. An operator can grasp the handle 112 between the proximal radial flange 602 and the distal radial flange 604 to move the assembled system 50. As shown, the proximal radial flange 602 can have a larger diameter than the distal radial flange 604.

To use a system 50 as described herein to drill articular cartridge proximate a defect, the distal tip 119 of the distal drill guide 118 can be placed perpendicular to a surface to be drilled. To facilitate stable placement of the distal drill guide 118 at the drilling surface, the handle device 100 can include a stabilization ring 502. The stabilization ring 502 can have a first outer diameter less than a second outer diameter of the distal drill guide 118, as shown in FIGS. 8A and 8B. The stabilization ring 502 can be placed perpendicular to the articular cartilage 306 and proximate a chondral defect. The handle device 100 can be advanced until the stabilization ring 502 is at least partially embedded within the articular cartilage 306 (e.g., until the larger diameter portion of the distal drill guide 118 is proximate the cartilage surface). Embedding the stabilization ring 502 can help prevent the distal drill guide 118 from moving laterally while drilling the defect. The distal tip of the stabilization ring 502 can be sharp so as to help facilitate the embedding within the cartilage.

In some examples, the distal drill guide 118 can include a taper 504. For example, a first diameter of the distal drill guide 118 proximate the handle 112 can be greater than a second diameter of the distal drill guide 118 at a distal tip 119, as shown in FIGS. 8A and 8B. The taper 504 can also provide ergonomic benefits by providing a larger area to grasp the handle device 100 at a proximate end, while providing a smaller cross section proximate the distal end of the handle device 100 to provide visibility of the drilling area. The taper can be approximately 1-20° (for example) 5-15° and approximately 1-5 cm long.

In some examples, the distal drill guide 118 can include one or more distal drill guide aperture 506. The aperture 506 can extend through an outer wall of the distal drill guide 118, as shown. The aperture 506 can enable tissue and aspiration fluid to exit the distal drill guide as cartilage is being drilled. For example, as tissue is being drilled by the threads 302 of the drill bit 300, tissue can travel proximally though the cannulated system (e.g., internal cannulation 122 of the handle device 100). The aperture 506 can provide a route for the tissue debris to exit the distal drill guide 118 instead of travelling up the internal cannulation 122. This can help to prevent under drilling using the system 50. For example, if the tissue debris travels proximally through the internal cannulation 122, it can exit the proximal end of the handle device 100 and wedge between the drill collar 102 and the disk 104, thereby preventing the drill collar 102 from fully seating on the disk 104—i.e., leaving the drill bit 300 proud.

Figure 9B:
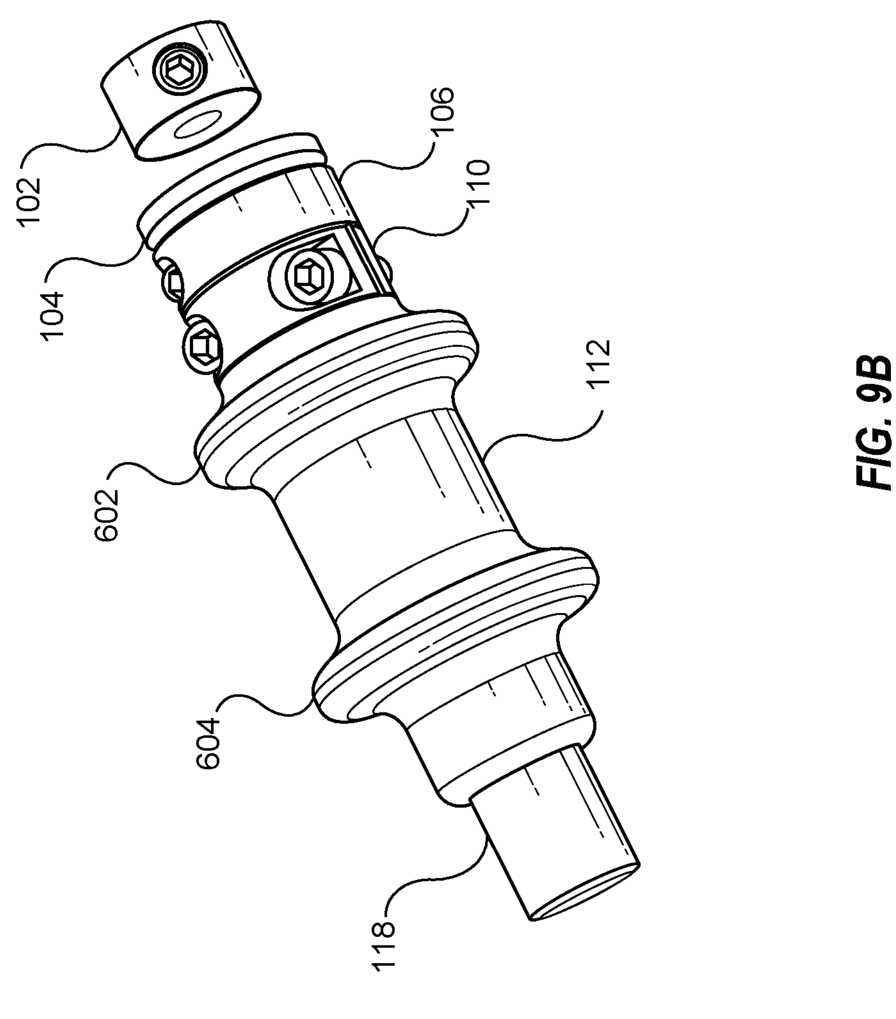
FIGS. 9A and 9B depict an unassembled example drilling system.
Figure 9A:
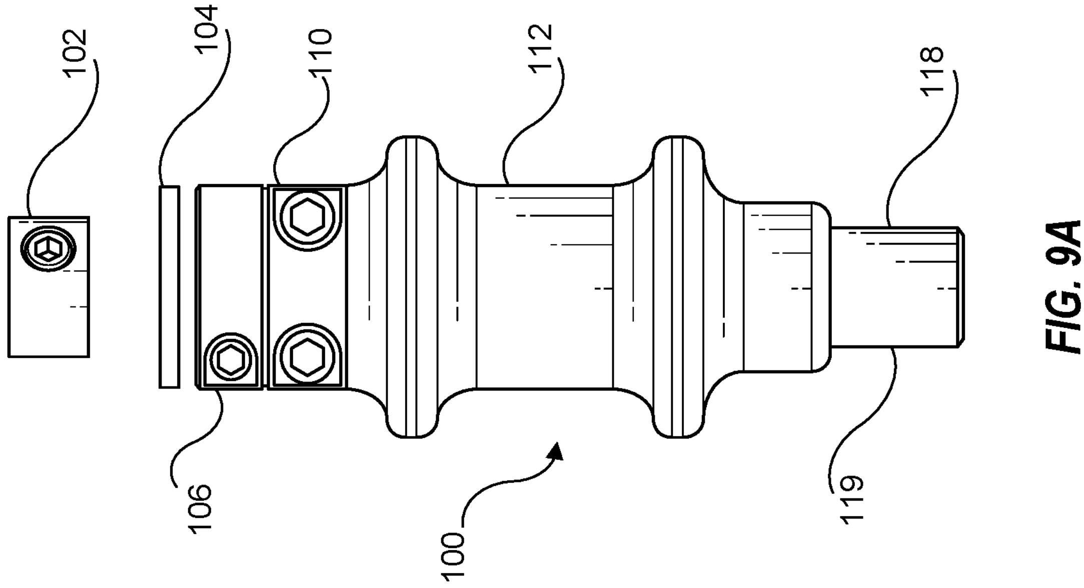

FIGS. 9A and 9B depict an unassembled example drilling system 50. The handle device 100 shows an example wherein the proximal radial flange 602 and the distal radial flange 604 can have the same outer diameter. In addition, the system 50 provides an example wherein the disk 104 is a flat, rotatable disk that does not include bearings (e.g., bearings 124 shown in FIG. 2).

Figures 10A, 10B, 10C:
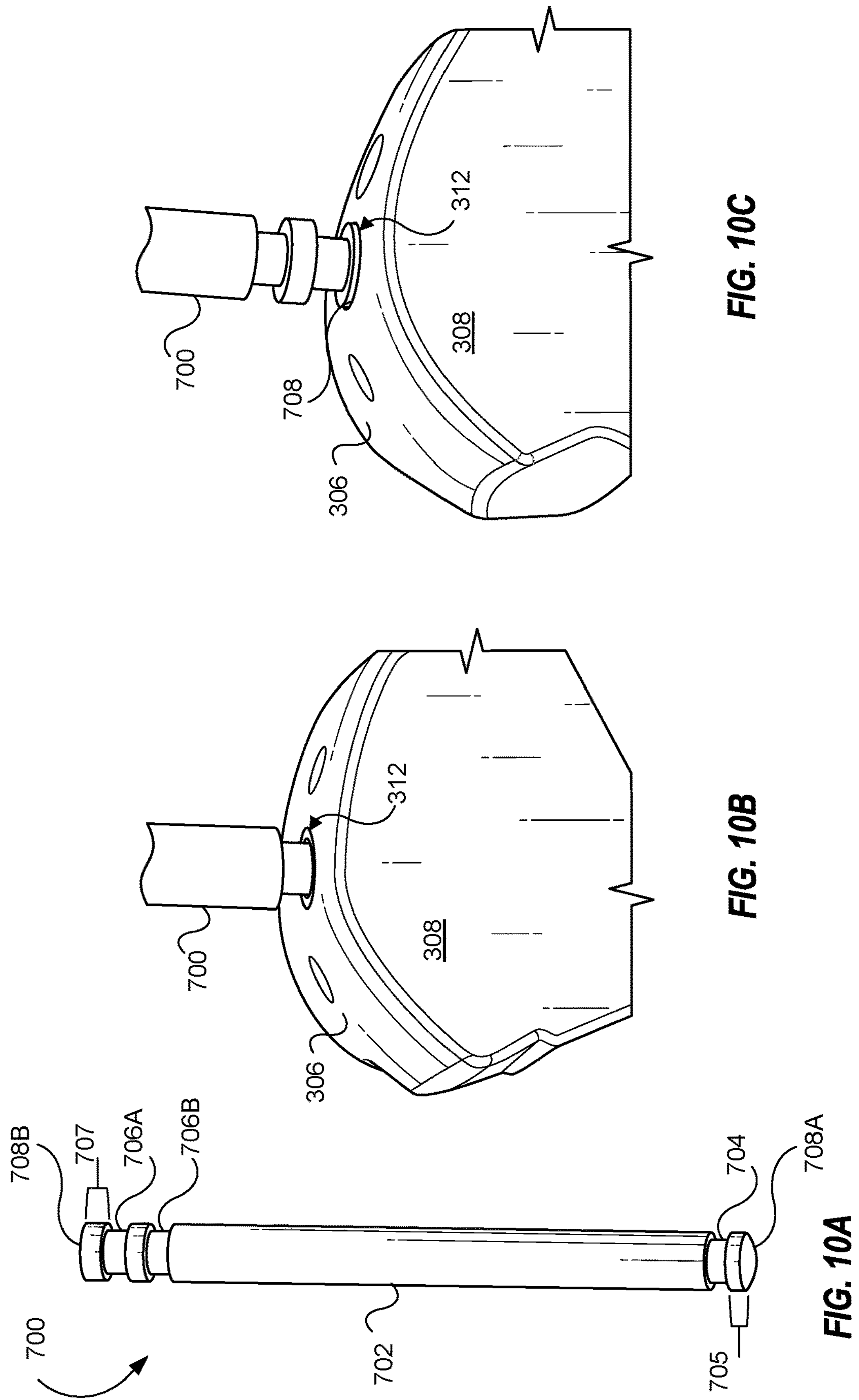
FIG. 10A depicts a double sided measuring guide.
FIG. 10B depicts a close-up of an example first measuring height of a double sided measuring guide being used to measure a defect site.
FIG. 10C depicts a close-up of an example second measuring height of a double sided measuring guide being used to measure the defect site in FIG. 10B.

FIG. 10A depicts a double sided measuring guide 700; FIG. 10B depicts a close-up of an example first measuring height 705 of a double sided measuring guide 700 being used to measure a defect site; and FIG. 10C depicts a close-up of an example second measuring height 707 of a double sided measuring guide 700 being used to measure the defect site in FIG. 10B. The double sided measuring guide 700 shown in these figures can be used in addition to or as an alternative to the measuring guides 200 (e.g., first measuring guide 202 and second measuring guide 204) shown in FIGS. 6A-7B. The double sided measuring guide 700 can include a shaft 702 connecting a first end and a second end. At the first end (shown at the bottom of FIG. 10A), the double sided measuring guide 700 can include a first depth indicator 704. The measuring indicator can provide a visual guide to the thickness (e.g., first measuring height 705) of a first tip 708A of the double sided measuring guide 700. The first depth indicator 704 can be a single ring (as shown), a notch, or text indicating the height of the first measuring height 705. Using an example to illustrate, the first measuring height 705 can have a 1.5 mm tip 708A thickness. At the second end (shown at the top of FIG. 10A), the double sided measuring guide 700 can include a second depth indicator (shown as a fist ring 706A and second ring 706B in FIG. 10A, collectively referred to as "second depth indicator 706"). The measuring indicator can provide a visual guide to the thickness (e.g., second measuring height 707) of a second tip 708B of the double sided measuring guide 700. The second depth indicator 706 can include rings (as shown), one or more notches, or text indicating the height of the second measuring height 707. Using an example to illustrate, the second measuring height 707 can have a 2.0 mm tip 708B thickness.

FIGS. 10B and 10C depict the double sided measuring guide 700 of FIG. 10A, and demonstrate how the double sided measuring guide 700 can be used to determine whether the defect depth is below or greater than the known thickness of the guides. Referring to FIG. 10B, the image shows the first tip 708A having a first measuring height 705 (e.g., 1.5 mm in this example) placed into a defect created by drilling. As can be seen, the first tip 708A sits flush with the defect or recessed slightly, showing that the defect is approximately 1.5 mm in depth. In FIG. 10C, the image shows the second tip 708B having a second measuring height 707 (e.g., 2.0 mm in this example) placed into the defect. As can be seen, the second tip 708B protrudes slightly from the defect, showing the defect is less than 2.0 mm in depth.

The tips (e.g., first tip 708A and second tip 708B) of the double sided measuring guide 700 can have a convex bevel to match the geometry of the defect created by bit 300. In some examples, the tips can include grooves (e.g., grooves 208 in FIGS. 6A and 6B) extending radially along the surface of the tips to facilitate removal of any bone, cartilage, or other tissue debris within the drilled defect. The double sided measuring guide 700 can be made of moldable plastics, metals, and/or the like. In some examples, the double sided measuring guide 700 can include radiopaque markers so that they are visible under fluoroscopy if inadvertently dropped into an incision of a patient.

Figure 11:
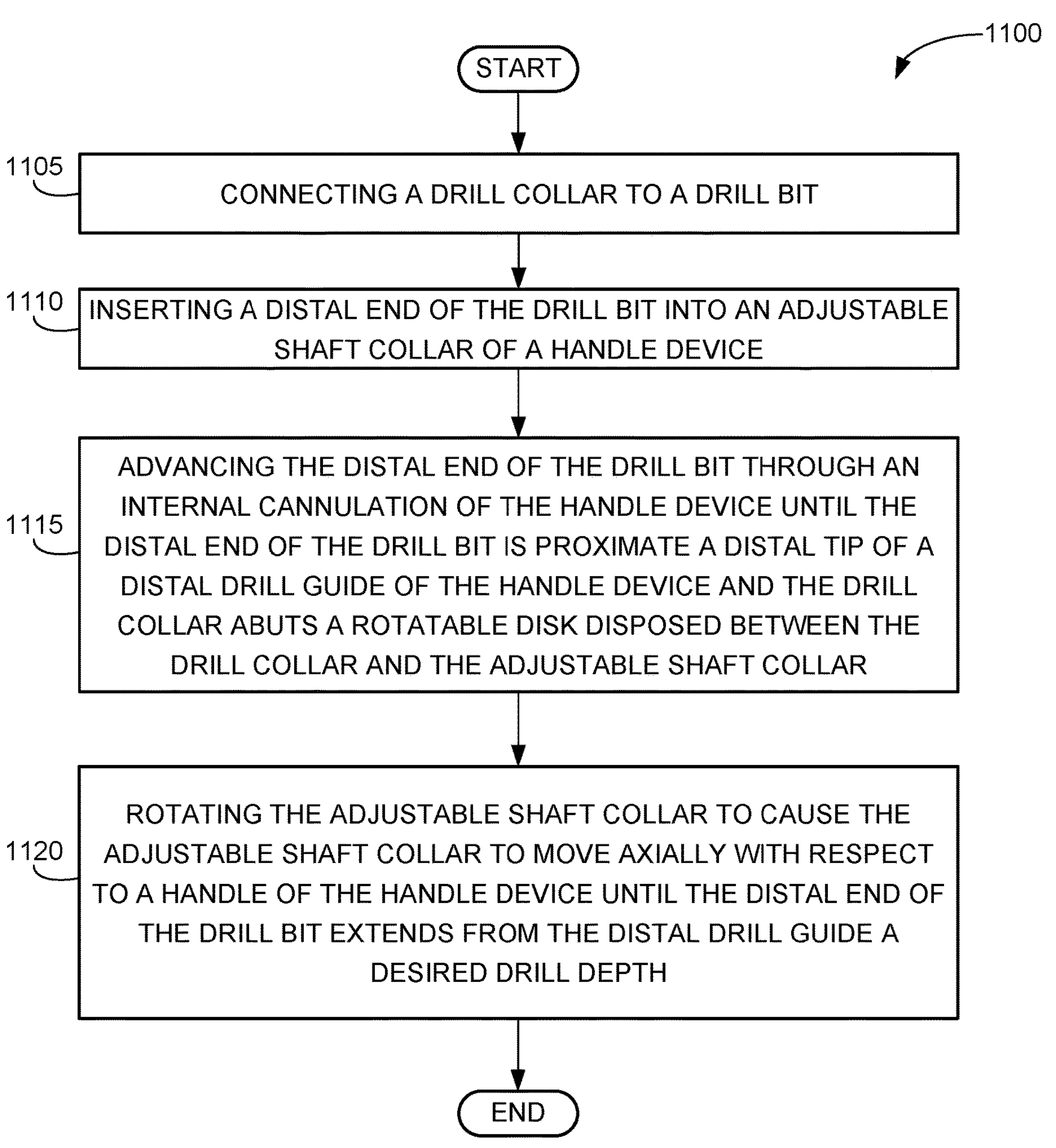
FIG. 11 is a flowchart depicting an example method for preparing articular cartilage for receiving a graft tissue.

FIG. 11 is a flowchart depicting a method 1100 for preparing articular cartilage for receiving a graft tissue, according to the present disclosure. The method 1100 can be performed by the example drilling systems 50 described herein. The method 1100 can begin by connecting 1105 a drill collar (e.g., drill collar 102) to a drill bit (e.g., drill bit 300). Once the drill collar is connected, the distal end of the drill bit can be inserted 1110 into an adjustable shaft collar (e.g., adjustable shaft collar 106) of a handle device (e.g., handle device 100). The distal end of the drill bit can be advanced 1115 through an internal cannulation (e.g., internal cannulation 122) of the handle device until (i) the distal end of the drill bit is proximate a distal tip of a distal drill guide (e.g., distal tip 119 of the distal drill guide 118) of the handle device and (ii) the drill collar abuts a rotatable disk (e.g., disk 104) disposed between the drill collar and the adjustable shaft collar. The adjustable shaft collar can be rotated 1120 to cause the adjustable shaft collar to move axially with respect to a handle (e.g., handle 112) of the handle device until the distal end of the drill bit extends from the distal drill guide a desired drill depth.

In comparison to prior approaches, it should be understood that dental drills have been used to create shallow osteochondral defects (e.g., up to 3 mm depth in rodent models). However, prior art dental drills are not available with drill size greater than 3 mm diameter, thus making them not suitable for creating shallow defects with larger diameters. Similarly, the OATS® Technique and corresponding instrumentation by Arthrex®, has been commonly used to create osteochondral defects for clinical applications and comes with various diameters. While the surgical tool associated with OATS shows success in creating defects with depth >6 mm when empirical methods of measuring defect depth is used, the solutions of this disclosure can provide more effective and more precise drilling and measurement. Moreover, conventional approaches fail to show any efficacy in creating shallow defects such as <3.0 mm where greater precision is required.

In contrast, the drilling devices and systems disclosed herein can be used with the OATS drilling bit as well as other drill bits, thus making the system 50 suitable for additional surgical applications. More importantly, the drilling devices and systems of this disclosure enable the operator to control and limit the drilling depth to be within a narrow range (<2.0 mm) when creating defects with larger diameter (6 mm-40 mm). The drilling devices and systems of this disclosure can be beneficial when the defect is created only on the articular cartilage surface and not into the subchondral bone. In some examples, the drilling device and system of this disclosure can be beneficial when a precise defect is needed to be created from the articular surface into the calcified cartilage region of the subchondral bone without reaching the porous bone marrow regions (e.g., cancellous bone).

The drilling devices and systems of this disclosure are also particularly suited for osteochondral allograft implantation, which are commonly used to treat large advanced stage cartilage legions. The diameter of the osteochondral allograft is determined based on the size of the cartilage lesion. The entire region of damaged tissue can be selected to be removed and replaced with allograft tissue, while minimizing removal of healthy tissue. A cylindrical osteochondral allograft can be obtained from a tissue bank or fabricated from an allograft condyle block. There is flexibility in the total height of the osteochondral allograft with either source. The allografts can be trimmed to be smaller, by removing bone from the end the allograft opposite the cartilage layer. Osteochondral allografts are typically between 5-20 mm in height and are measured using a ruler with millimeter markings.

A recipient site can be created in the patient by removing both bone and cartilage tissue by using a drill or biopsy punch, to the desired depth, based on the allograft thickness. The diameter of the drill or punch tool depends on the size of the unhealthy cartilage, to match the osteochondral allograft. The depth of the recipient site must match the height of the osteochondral allograft. This can be done in either order, e.g., the allograft can be prepared, height measured, and then the recipient site depth can be targeted to match, or the recipient site can be prepared, depth measured, and then the allograft of proper height can be prepared. The height of the osteochondral allograft must match the recipient site depth to ensure the allograft will be flush in the defect. The flushness of the implanted allograft is critical to its long-term performance.

Current methods of recipient site creation rely on millimeter scale measurements and visual estimations. In some examples, to achieve an ideal depth, the drilling process can be repeated, if the depth is not initially reached. The millimeter markings on the recipient site creation tool can be difficult to see while creating the recipient site. Following generation of the site, other measurement tools can be utilized, but this can be only be done following irreversible site creation. In contrast, the solutions of this disclosure allow the desired depth of the recipient site to be precisely pre-set, prior to recipient site creation. The drilling device prevents excess drilling past the programmed depth. The set depth can be programmed with 50 μm of resolution. Additionally, although the drilling depth is pre-set, the depth of the drilling guide can still be adjusted during surgery on site, if alternative depth is required.

In some examples, the device and system can be used in connection with tissue engineered osteochondral graft or synthetic osteochondral graft implantation. Tissue engineered osteochondral and/or synthetic osteochondral grafts often have predetermined size (e.g., 15 mm deep). Current drilling methods use tick mark(s) on the drill bit and a depth guide to measure the depth. However, the previous method can only measure the depth after the defect has been drilled. In the case of over drilling, the process cannot be undone. In contrast, the solutions of this disclosure allow the operator to adjust the drill to the desired depth before drilling. During drilling, the drilling device can be equipped with the indicator part (e.g., disk 104), that alerts the operator and stops the drill bit penetration once the preset depth has been reached. The tissue engineered osteochondral graft or synthetic osteochondral graft with the matched preset depth can then be implanted to have an articular surface match to the surrounding tissue.

The specific configurations, choice of materials and the size and shape of various elements can be varied according to particular design specifications or constraints requiring a system or method constructed according to the principles of the disclosed technology. Such changes are intended to be embraced within the scope of the disclosed technology. The presently disclosed embodiments, therefore, are considered in all respects to be illustrative and not restrictive. It will therefore be apparent from the foregoing that while particular forms of the disclosure have been illustrated and described, various modifications can be made without departing from the spirit and scope of the disclosure and all changes that come within the meaning and range of equivalents thereof are intended to be embraced therein.

What is claimed is:

1. A system to remove portions of articular cartilage, the system comprising:
- a handle device, comprising:
  - a handle;
  - an adjustable shaft collar rotatable to adjust a drill set distance between the adjustable shaft collar and the handle; and
  - a distal drill guide extending from the handle at an end opposite the adjustable shaft collar;
- a drill collar attachable to a drill bit and configured to remain stationary along a length of the drill bit once attached; and
- a rotatable disk positionable between the adjustable shaft collar and the drill collar, the rotatable disk including a central hole sized to accept the drill bit.

2. The system of claim 1, further comprising the drill bit.

3. The system of claim 2, wherein a diameter of the drill bit ranges from 3.0 mm to 40.0 mm.

4. The system of claim 2, wherein a diameter of the drill bit ranges from 3.0 mm to 10.0 mm.

5. The system of claim 2, wherein a diameter of the drill bit is at least 3.0 mm.

6. The system of claim 2, wherein a diameter of the drill bit is no greater than 40 mm.

7. A kit including the components of claim 2.

8. The system of claim 1, wherein the rotatable disk comprises a plurality of bearings.

9. The system of claim 8, wherein the rotatable disk is a thrust bearing or an axial needle roller disk and the bearings are arranged radially around a circumference of the rotatable disk.

10. The system of claim 1, wherein the drill collar comprises a collar set screw configured to abut the drill bit to attach the drill collar thereto.

11. The system of claim 1, wherein the handle comprises a handle grasping indentation shaped to correspond to a location of a thumb of a user.

12. The system of claim 11, wherein the handle comprises a handle distal flange comprising a finger stop for the user.

13. The system of claim 1, wherein the handle comprises a proximal radial flange and a distal radial flange comprising one or more locations for grasping the handle.

14. The system of claim 1, wherein the distal drill guide comprises:

a stabilization ring positioned at a distal end of the distal drill guide, the stabilization ring comprising a first outer diameter less than a second outer diameter of the distal drill guide proximal to the stabilization ring, wherein the stabilization ring is configured to insert into articular cartilage to provide lateral stability for the distal drill guide.

15. The system of claim 1, wherein the distal drill guide comprises a taper, such that a first diameter of the distal drill guide proximate the handle is greater than a second diameter of the distal drill guide at a distal tip of the distal drill guide.

16. The system of claim 15, wherein the taper is 1 to 15° and 1 to 5 cm long.

17. The system of claim 1, wherein the distal drill guide comprises one or more apertures extending through an outer wall of the distal drill guide and configured to enable tissue and aspiration fluid to exit the distal drill guide as cartilage is being drilled.

18. The system of claim 1, further comprising a first measuring guide having a first measuring thickness and a second measuring guide having a second measuring thickness.

19. The system of claim 18, wherein the first measuring guide and the second measuring guide both comprise a distal convex bevel configured to match a geometry of a defect created by the drill bit.

20. The system of claim 18, wherein the first measuring guide and the second measuring guide both comprise radial grooves configured to remove debris from a defect created by the drill bit as the respective measuring guide is rotated within the defect.

21. A kit including the components of claim 18.

22. The system of claim 1, further comprising a double sided measuring guide comprising a first end having a first depth indicator and a second end having a second depth indicator.

23. A kit including the components of claim 22.

24. The system of claim 1, wherein a 90-degree turn of the adjustable shaft collar with respect to the handle is equivalent to a 200 μm change in the drill set distance.

25. The system of claim 1, wherein the adjustable shaft collar is configured to adjust the drill set distance from between 0.00 mm and 20.00 mm.

26. The system of claim 1, wherein the adjustable shaft collar is configured to adjust the drill set distance from between 20.00 mm and 0.00 mm.

27. A kit including the components of claim 1.

28. A method of drilling a circular cavity in articular cartilage using the system of claim 1.

29. A method of preparing articular cartilage for receiving a graft tissue, comprising:

connecting a drill collar to a drill bit;

inserting a distal end of the drill bit into an adjustable shaft collar of a handle device;

advancing the distal end of the drill bit through an internal cannulation of the handle device until the distal end of the drill bit is proximate a distal tip of a distal drill guide of the handle device and the drill collar abuts a rotatable disk disposed between the drill collar and the adjustable shaft collar; and rotating the adjustable shaft collar to cause the adjustable shaft collar to move axially with respect to a handle of the handle device until the distal end of the drill bit extends from the distal drill guide a desired drill depth.

30. The method of claim 29, further comprising:

retracting the drill bit from the internal cannulation such that the distal end of the drill bit does not extend from a distal tip of the distal drill guide;

placing the distal tip of the distal drill guide perpendicular to a surface to be drilled; and advancing the drill bit through the internal cannulation of the handle device until the drill collar contacts the adjustable shaft collar.

31. The method of claim 30, wherein the surface is articular cartilage, and wherein the distal end of the drill bit is advanced proximate to subchondral bone.

32. The method of claim 30, further comprising removing a cannulation remnant from a circular defect created by the drill bit using a bone nipper or biopsy punch, wherein the drill bit is cannulated.

33. The method of claim 30, further comprising:

removing the drill bit and handle device from the surface;

inserting a first measuring guide into a circular defect created by the drill bit; and measuring a depth of the circular defect using a first tip of the first measuring guide.

34. The method of claim 33, further comprising:

removing the first measuring guide from the circular defect;

inserting a second measuring guide into the circular defect; and measuring the depth of the circular defect using a second tip of the second measuring guide.

35. The method of claim 33, further comprising:

rotating the first measuring guide to remove tissue within the circular defect with radial grooves disposed on the first tip of the first measuring guide.

36. The method of claim 33, wherein the first tip of the first measuring guide comprises a convex bevel to match the circular defect.

37. The method of claim 30, further comprising:
removing the drill bit and handle device from the surface;
inserting a first end of a double sided measuring guide into a circular defect created by the drill bit, the first end having a first measuring height;
measuring a depth of the circular defect using the first end of the double sided measuring guide;
removing the double sided measuring guide from the circular defect;
rotating the double sided measuring guide end for end;
inserting a second end of the double sided measuring guide into the circular defect, the second end having a second measuring height different than the first measuring height; and
measuring the depth of the circular defect using the second end of the double sided measuring guide.

38. The method of claim 37, wherein the first end of the double sided measuring includes a first depth indicator, and wherein the second end of the double sided measuring includes a second depth indicator.

39. The method of claim 29, further comprising:
retracting the drill bit from the internal cannulation such that the distal end of the drill bit does not extend from a distal tip of the distal drill guide;
placing a stabilization ring of the distal tip of the distal drill guide perpendicular to articular cartilage and proximate a chondral defect; and
advancing the handle device until the stabilization ring is at least partially embedded within the articular cartilage.

40. The method of claim 29, further comprising removing tissue debris from a distal drill guide aperture disposed in an outer surface of the distal drill guide.

41. A kit for removing portions of articular cartilage, the kit comprising:
a handle device comprising:
a handle;
an adjustable shaft collar rotatable to adjust a drill set distance between the adjustable shaft collar and the handle; and
a distal drill guide extending from the handle at an end opposite the adjustable shaft collar;
a drill bit;
a drill collar attachable to the drill bit;
a rotatable disk positionable between the adjustable shaft collar and the drill collar, the rotatable disk including a central hole sized to accept the drill bit; and
a first measuring guide configured to measure a depth of a circular defect created by the drill bit.

42. The kit of claim 41, further comprising a second measuring guide, wherein the first measuring guide has a first measuring thickness and the second measuring guide has a second measuring thickness different than the first measuring thickness.

43. The kit of claim 42, wherein the first measuring guide and the second measuring guide both comprise a distal convex bevel matching a geometry of a defect created by the drill bit.

44. The kit of claim 42, wherein the first measuring guide and the second measuring guide both comprise radial grooves configured to remove debris from a defect created by the drill bit as the respective measuring guide is rotated within the defect.

45. The kit of claim 41, wherein the first measuring guide is a double sided measuring guide comprising a first end having a first depth indicator and a second end having a second depth indicator.

* * * * *